(12) United States Patent
Hayakawa (10) Patent No.: US 8,876,752 B2
(45) Date of Patent: Nov. 4, 2014

(54) DIALYSIS CATHETER

(75) Inventor: Toshinobu Hayakawa, Fukuroi (JP)

(73) Assignee: Covidien LP, Mansfield, MA (US)

( * ) Notice: Subject to any disclaimer, the term of this patent is extended or adjusted under 35 U.S.C. 154(b) by 524 days.

(21) Appl. No.: 13/234,605

(22) Filed: Sep. 16, 2011

(65) Prior Publication Data

US 2012/0245513 A1    Sep. 27, 2012

(30) Foreign Application Priority Data

Sep. 24, 2010    (JP) ................... 2010-213347

(51) Int. Cl.
- *A61M 1/00* (2006.01)
- *A61M 1/36* (2006.01)
- *A61M 25/00* (2006.01)

(52) U.S. Cl.
CPC .......... *A61M 1/3653* (2013.01); *A61M 25/0068* (2013.01); *A61M 25/003* (2013.01); *A61M 2025/0031* (2013.01)
USPC .............................................. 604/29; 604/43

(58) Field of Classification Search
CPC ............. A61M 2025/0031; A61M 2025/0037; A61M 25/0029; A61M 1/285; A61M 25/0028; A61M 1/3653; A61M 2001/3661
USPC ...................................................... 604/43, 29
See application file for complete search history.

(56) References Cited

U.S. PATENT DOCUMENTS

| | | | |
|---|---|---|---|
| 2,972,779 A | 2/1961 | Cowley | |
| D208,838 S | 10/1967 | St. Amand | |
| 4,134,402 A | 1/1979 | Mahurkar | |
| D254,270 S | 2/1980 | Ziegler | |
| D272,651 S | 2/1984 | Mahurkar | |
| 4,443,333 A | 4/1984 | Mahurkar | |
| 4,568,329 A | 2/1986 | Mahurkar | |
| 4,583,968 A | 4/1986 | Mahurkar | |
| 4,682,978 A | 7/1987 | Martin | |
| 4,692,141 A | 9/1987 | Mahurkar | |
| 4,770,652 A | 9/1988 | Mahurkar | |
| D298,461 S | 11/1988 | Manno | |
| 4,808,155 A | 2/1989 | Mahurkar | |
| 4,842,582 A | 6/1989 | Mahurkar | |

(Continued)

FOREIGN PATENT DOCUMENTS

| | | |
|---|---|---|
| CA | 2 389 227 | 5/2001 |
| DE | 41 05 965 | 8/1992 |

(Continued)

OTHER PUBLICATIONS

European Search Report from EP Application No. EP 12 18 3701 mailed Dec. 12, 2012.

(Continued)

*Primary Examiner* — Kevin C Sirmons
*Assistant Examiner* — Deanna K Hall
(74) *Attorney, Agent, or Firm* — John Paul Mello, Esq.

(57) ABSTRACT

A dialysis catheter is provided which makes it possible to improve patency without reducing the ease of insertion, while also making it possible to effectively suppress the "clinging phenomenon". The dialysis catheter has a first portion provided with a thickened part which increases the thickness of the peripheral wall of a blood feed lumen on the blood removal lumen side thereof, and the cross-sectional area of the first portion is smaller than the cross-sectional area of a second portion.

4 Claims, 11 Drawing Sheets

(56) References Cited

U.S. PATENT DOCUMENTS

| | | |
|---|---|---|
| 4,883,426 A | 11/1989 | Ferrer |
| 4,894,057 A | 1/1990 | Howes |
| 4,904,238 A | 2/1990 | Williams |
| 5,009,636 A | 4/1991 | Wortley et al. |
| 5,167,623 A | 12/1992 | Cianci et al. |
| 5,209,723 A | 5/1993 | Twardowski et al. |
| 5,221,256 A | 6/1993 | Mahurkar |
| 5,374,245 A | 12/1994 | Mahurkar |
| 5,395,315 A | 3/1995 | Griep |
| 5,403,291 A | 4/1995 | Abrahamson |
| 5,405,320 A | 4/1995 | Twardowski et al. |
| 5,405,341 A | 4/1995 | Martin |
| 5,419,777 A | 5/1995 | Hofling |
| 5,451,216 A | 9/1995 | Quinn |
| 5,486,159 A | 1/1996 | Mahurkar |
| 5,536,234 A | 7/1996 | Newman |
| 5,549,541 A | 8/1996 | Muller |
| 5,554,136 A | 9/1996 | Luther |
| 5,569,182 A | 10/1996 | Twardowski et al. |
| 5,571,093 A | 11/1996 | Cruz et al. |
| 5,685,867 A | 11/1997 | Twardowski et al. |
| 5,725,495 A | 3/1998 | Strukel et al. |
| 5,785,678 A | 7/1998 | Griep et al. |
| 5,830,196 A | 11/1998 | Hicks |
| 5,961,486 A | 10/1999 | Twardowski et al. |
| 6,086,565 A | 7/2000 | Ouchi |
| 6,409,700 B1 | 6/2002 | Siegel, Jr. et al. |
| 6,517,529 B1 | 2/2003 | Quinn |
| 6,786,884 B1 | 9/2004 | DeCant, Jr. et al. |
| 6,945,951 B1 | 9/2005 | Bonnette et al. |
| 6,991,625 B1 * | 1/2006 | Gately et al. .................. 604/523 |
| 7,025,751 B2 | 4/2006 | Silva et al. |
| 7,066,914 B2 | 6/2006 | Andersen |
| 7,141,035 B2 | 11/2006 | Haggstrom |
| 7,182,746 B2 | 2/2007 | Haarala et al. |
| 7,223,263 B1 | 5/2007 | Seno |
| 7,322,953 B2 | 1/2008 | Redinger |
| 7,641,646 B2 | 1/2010 | Kennedy, II |
| 7,717,898 B2 | 5/2010 | Gately et al. |
| 7,776,005 B2 | 8/2010 | Haggstrom et al. |
| 8,007,488 B2 | 8/2011 | Ravenscroft |
| 8,092,415 B2 | 1/2012 | Moehle et al. |
| 2002/0156430 A1 | 10/2002 | Haarala et al. |
| 2002/0165492 A1 | 11/2002 | Davey et al. |
| 2005/0177094 A1 | 8/2005 | Igarashi et al. |
| 2005/0182352 A1 | 8/2005 | DiMatteo et al. |
| 2005/0182354 A1 | 8/2005 | Quinn |
| 2006/0253063 A1 | 11/2006 | Schweikert |
| 2009/0118661 A1 | 5/2009 | Moehle |
| 2009/0192435 A1 | 7/2009 | Gregersen |
| 2009/0216174 A1 | 8/2009 | Nardeo |
| 2010/0069818 A1 | 3/2010 | Smouse |
| 2010/0076404 A1 | 3/2010 | Ring |
| 2010/0081986 A1 | 4/2010 | Matson et al. |
| 2011/0130745 A1 | 6/2011 | Shevgoor et al. |

FOREIGN PATENT DOCUMENTS

| | | |
|---|---|---|
| EP | 0 555 780 | 8/1993 |
| EP | 1 407 798 | 4/2004 |
| EP | 1905476 A2 | 4/2008 |
| EP | 2119468 A1 | 11/2009 |
| EP | 2 168 625 | 3/2010 |
| EP | 2168625 A1 | 3/2010 |
| GB | 1 503 469 | 3/1978 |
| JP | H11-197238 A | 7/1999 |
| JP | 2001-340466 | 12/2001 |
| JP | 2004-174130 A | 6/2004 |
| JP | 2007-502678 | 2/2007 |
| JP | 2007-521913 | 8/2007 |
| WO | WO 92/14500 | 9/1992 |
| WO | WO 99/38550 | 8/1999 |
| WO | WO 2004/096334 A1 | 11/2004 |
| WO | WO 2006/126642 | 11/2006 |
| WO | 2007/111874 A2 | 10/2007 |
| WO | 2008155145 A1 | 12/2008 |
| WO | WO 2009/052506 A1 | 4/2009 |
| WO | 2009131583 A1 | 10/2009 |

OTHER PUBLICATIONS

European Search Report from EP Application No. EP 12 18 4079 mailed Dec. 12, 2012.
European Search Report from EP Application No. EP 11 18 2128 dated Mar. 3, 2012.
First Office Action issued in Chinese Appl. No. 201210059962.5 dated Apr. 26, 2013.
Office Action issued in Japanese Application No. 2012-212145 mailed Aug. 28, 2013.
Official Action issued in Japanese Appl. No. 2012-214681 dated Aug. 28, 2013.
Examiner's Report issued in Australian Appl. No. 2012230094 dated Sep. 12, 2013.
Examiner's Report issued in Australian Appl. No. 2010226891 dated Sep. 5, 2013.

* cited by examiner

DIALYSIS CATHETER

CROSS-REFERENCE TO RELATED APPLICATIONS

This application claims priority under 35 U.S.C. §119 to Japanese Patent Application Serial No. 2010-213347, filed Sep. 24, 2010, the entire contents of which are incorporated herein by reference in their entirety.

TECHNICAL FIELD

The present disclosure relates to a dialysis catheter having an improved shape at the tip-end side.

DESCRIPTION OF RELATED ART

Therapy employing artificial dialysis is conventionally carried out when renal function has become insufficient due to illnesses such as renal failure, for example. Blood dialysis is one such form of artificial dialysis which is generally carried out by withdrawing (removing) blood to outside the body (to a dialysis circuit) using a dialysis catheter, removing waste products and toxins in the dialysis circuit, and then delivering (feeding) this blood into a blood vessel to circulate some of the patient's blood. Ensuring a stable and adequate amount of blood flow leads to an improved dialysis effect in blood dialysis.

During usage, the dialysis catheter is made indwelling in a large-diameter blood vessel which has a plentiful flow of blood, such as the femoral vein or the subclavian vein, using a guidewire which guides the catheter, or a stylet for increasing the rigidity of the catheter, into the blood vessel, for example, in such a way that the tip end of the catheter is oriented in the same direction as the blood flow. The following requirements are important in this kind of dialysis catheter: (1) ease of insertion; (2) high patency; and (3) unlikely occurrence of the "clinging phenomenon" which causes blood removal failure.

"Ease of insertion" in (1) concerns low insertion resistance of the dialysis catheter. "High patency" in (2) concerns the fact that the blood removal opening or lumen is not readily closed off by a blood clot or fibrin sheath, or that the blood clot or fibrin sheath can be easily removed even if closure does occur. "Unlikely occurrence of the 'clinging phenomenon'" in (3) concerns the fact that the blood removal lumen does not readily attach to the wall of the blood vessel where the catheter is placed by way of the blood feed opening. In other words, the more of requirements (1) to (3) which are satisfied, the more it is possible to reduce the burden on the practitioner and the patient, and a more stable rate of blood flow can be achieved.

Double-lumen catheters of the side-hole type which are double-axial type catheters are often used as dialysis catheters employed in blood dialysis. In this type of catheter the internal cavity is divided into a two-layer lumen, namely a blood removal lumen and a blood feed lumen, and a blood removal opening (blood removal hole) is provided on the outer peripheral surface of the catheter as a side hole. Furthermore, double-lumen catheters other than this are also in widespread use, such as double-axial type end-hole type catheters in which blood removal and blood feed openings (blood removal hole and blood feed hole) are respectively provided at the tip-end side of the catheter body, or coaxial type catheters in which an inner catheter is detachably fitted in the lumen of an outer catheter.

However, even though side-hole type double-lumen catheters can be inserted very easily into the body, they have the features of poorer patency than end-hole type catheters and there is a greater likelihood of the "clinging phenomenon" occurring. Proposals have therefore been made for various kinds of double-lumen catheters employing an end-hole type catheter which is improved in such a way that the patency is improved and the occurrence of the "clinging phenomenon" is suppressed with the aim of reducing the burden on the practitioner and the patient and allowing a stable blood flow rate to be achieved.

One such proposal concerns: "A double-lumen catheter in which a tube having a blood return lumen and a blood removal lumen partitioned by a dividing wall forms the catheter body, wherein a blood return hole constituting an opening in the blood return lumen is provided in the region of the tip end of the catheter body, and a blood removal hole constituting an opening in the blood removal lumen is provided at a position which is 3-11 cm away from the tip end of the catheter body towards the base thereof; the open surface of the blood removal hole is angled at 5-90° with respect to the lengthwise direction of the catheter body, and the shape of the catheter body from the position of the blood removal hole to the tip-end side comprises a narrow-diameter section of small cross-sectional area and a broad-diameter section of large cross-sectional area which is a continuation thereof" (see JP Application Publication 2001-340466, for example).

Another proposal concerns: "A double lumen dialysis catheter, comprising a unitary straight [sic], an internal divider extending along a longitudinal portion of said tube and forming said tube into a blood intake lumen and a blood return lumen, one end of said blood return lumen extending beyond the associated end of said blood inlet lumen a distance sufficient to prevent mixing of the returned blood with the blood taken in, the distal end of said blood inlet lumen terminating rearward of the juncture of the blood return lumen bevel and the associated lumen periphery, each of said lumens defining blood flow paths one parallel to the other along the entire length thereof and at the ends thereof such that blood entering said intake lumen and blood leaving said return lumen enter and exit the associated blood vessel in a direction substantially parallel to the vessel wall" (see PCT Application JP 2007-502678, for example).

A further proposal concerns: "A distal tip for a catheter comprising: first and second lumens extending therethrough, wherein in an operative configuration, the first and second lumens are coupled to first and second lumens of a dual lumen catheter; a first opening fluidly connected to the first lumen for inflow of fluid from a body lumen into which the distal tip is inserted in a normal mode of operation and for outflow of fluid thereto in a reverse mode of operation; a second opening fluidly connected to the second lumen, the second opening being disposed distally from the first opening and separated therefrom by a selected stagger distance for outflow of fluid therefrom when the catheter is in the normal mode of operation and for inflow of fluid from the body lumen in a reverse mode of operation; a contoured flow deflection element directing, in the reverse mode of operation, outflow from the first opening away from the second opening; and a contoured outlet portion of the second opening reducing an outflow velocity therefrom in the normal mode of operation (see PCT Application JP 2007-521913, for example).

The end-hole type double-lumen catheters disclosed in the Japanese Patent Documents discussed above have an improved structure at the tip-end side of the catheter. However, with the double-lumen catheter disclosed in JP Application Publication 2001-340466, resistance is produced when the blood removal hole (blood removal hole 3a) is inserted into the body, and the insertion resistance is very large. Furthermore, there is still a possibility of the "clinging phenomenon" occurring when use is made of the double-lumen catheter disclosed in JP Application Publication 2001-340466.

Furthermore, with the double-lumen catheter disclosed in PCT Application JP 2007-502678, resistance is produced when the expanded bevel and the intake opening of the blood intake lumen are inserted into the body, and the insertion resistance is very large. Furthermore, there is still a possibility of the "clinging phenomenon" occurring when use is made of the double-lumen catheter disclosed in PCT Application JP 2007-502678, in the same way as with the double-lumen catheter disclosed in JP Application Publication 2001-340466.

Furthermore, with the double-lumen catheter disclosed in PCT Application JP 2007-521913, resistance is produced when the control element (control element 122) and the orifice (orifice 112) are inserted into the body, and the insertion resistance is very large. Furthermore, there is still a possibility of the "clinging phenomenon" occurring when use is made of the double-lumen catheter disclosed in PCT Application JP 2007-521913, in the same way as with the double-lumen catheters disclosed in JP Application Publication 2001-340466 and PCT Application JP 2007-502678.

SUMMARY

The present invention has been devised in order to resolve the problems outlined above, and the object thereof lies in providing a dialysis catheter which makes it possible to reduce insertion resistance when the catheter is inserted into the body and to improve patency, while also making it possible to effectively reduce the occurrence of the "clinging phenomenon".

The dialysis catheter according to the present disclosure is a dialysis catheter of the end-hole type which includes a catheter body provided with a blood feed lumen and a blood removal lumen partitioned by a dividing wall, in which the tip end of the blood removal lumen is positioned further towards the base end than the tip end of the blood feed lumen, a blood removal hole is formed at the tip end of the blood removal lumen, and a blood feed hole is formed at the tip end of the blood feed lumen. The catheter body includes: a first portion which includes the blood feed lumen and is formed to a prescribed length from the tip end within the area between the blood removal hole and the blood feed hole; a second portion including the blood feed lumen and the blood removal lumen, whereof the cross-sectional shape from the blood removal hole to the base end is substantially circular; and a third portion which includes the blood feed lumen and connects the first portion and the second portion. The first portion includes a thickened part which increases the thickness of the peripheral wall of the blood feed lumen on the blood removal lumen side, and the cross-sectional area of said first portion including the thickened part is less than the cross-sectional area of the second portion. The third portion includes an extension part having a substantially semicircular cross-sectional shape and including a flat surface part provided at the base-end side as an extension of the dividing wall and forming part of the peripheral wall of the blood feed lumen, and a curved surface part forming part of the peripheral wall of the blood feed lumen outside the dividing wall. The third portion also includes a connecting part for connecting the extension part and the first portion. When the catheter body is seen from the tip-end side, the top part of the thickened part on the first portion and the top part of the blood removal hole, which has a substantially semicircular cross section in the second portion, completely overlap each other.

In the dialysis catheter according to the present disclosure, the cross-section of the first portion has a substantially elliptical shape in which the major axis is substantially perpendicular to the dividing wall; and the major axis of the substantially elliptical shape is made to substantially coincide with the diameter of the cross-sectional shape of the second portion.

In the dialysis catheter according to the present disclosure, the connecting part of the third portion includes: a first inclined face which connects the area around the top part of the thickened part to the flat surface part of the extension part; and a second inclined face which connects the peripheral wall of the tip end, other than the area around the top part of the thickened part, to the curved surface part of the extension part.

In the dialysis catheter according to the present disclosure, the open face of the blood removal hole is inclined in such a way that the angle formed with the dividing wall is an acute angle.

In the dialysis catheter according to the present disclosure, when the catheter body is seen from the tip-end side, the top part of the thickened part on the first portion and the top part of the blood removal hole, which has a substantially semicircular cross section in the second portion, completely overlap each other, and therefore it is possible to reduce insertion resistance and improve patency, and the occurrence of the "clinging phenomenon" can be effectively suppressed. In particular, it is possible to prevent the open face of the blood removal hole from creating insertion resistance, and therefore it is possible to markedly suppress a reduction in ease of insertion of the catheter into the body.

In the dialysis catheter according to the present disclosure, the cross-section of the first portion has a substantially elliptical shape in which the major axis is substantially perpendicular to the dividing wall, and the major axis of the substantially elliptical shape is made to substantially coincide with the diameter of the substantially circular cross-sectional shape of the second portion, and therefore it is possible to cover the opening face of the blood removal hole without resorting to a complex shape.

In the dialysis catheter according to the present disclosure, the connecting part which forms the third portion includes a first inclined face which connects the area around the top part of the thickened part to the flat surface part of the extension part; and a second inclined face which connects the peripheral wall of the tip end, other than the area around the top part of the thickened part, to the curved surface part of the extension part, and therefore the first portion and the second portion make it possible to prevent the connecting part from creating insertion resistance. Furthermore, there is no need to resort to a complex shape.

In the dialysis catheter according to the present disclosure, the open face of the blood removal hole is inclined in such a way that the angle formed with the dividing wall is an acute angle, and therefore it is possible to further suppress a reduction in insertion resistance without resorting to a complex shape.

DESCRIPTION OF THE EMBODIMENTS

A mode of embodiment of the present disclosure will be described below with reference to the figures.

Figure 1:
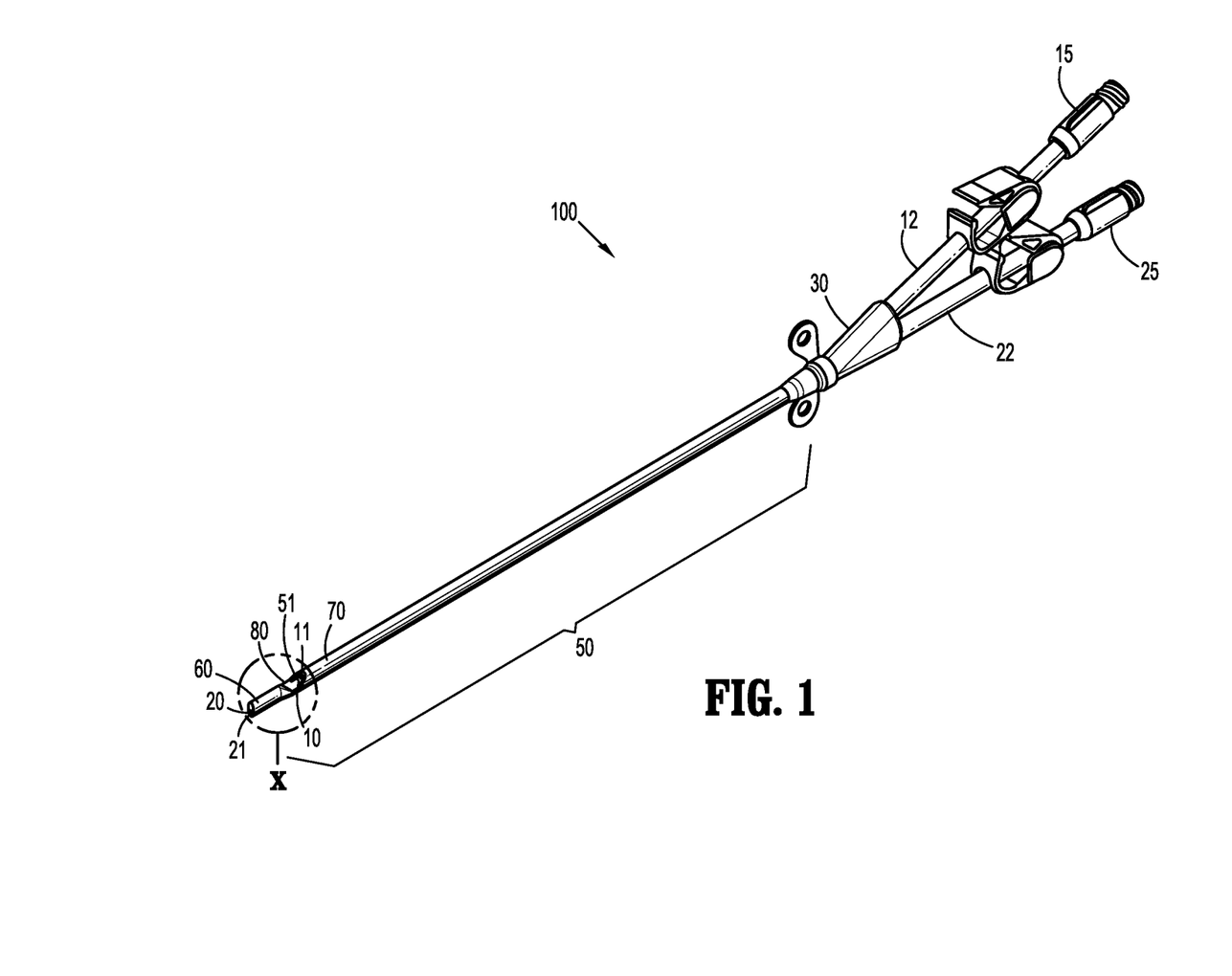
FIG. 1 is an oblique view showing the overall structure of the dialysis catheter according to a mode of embodiment of the present disclosure.
Figure 2:
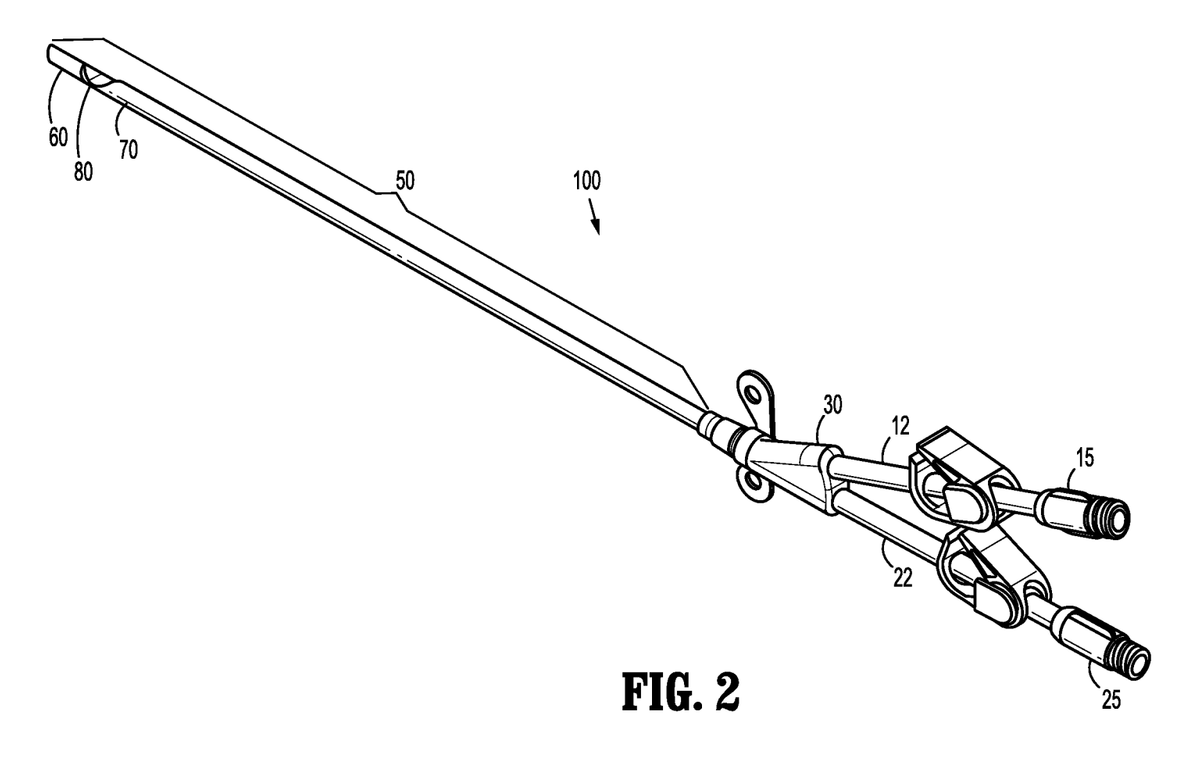
FIG. 2 is an oblique view seen from a different angle of the overall structure of the dialysis catheter as shown in FIG. 1.
Figure 3:
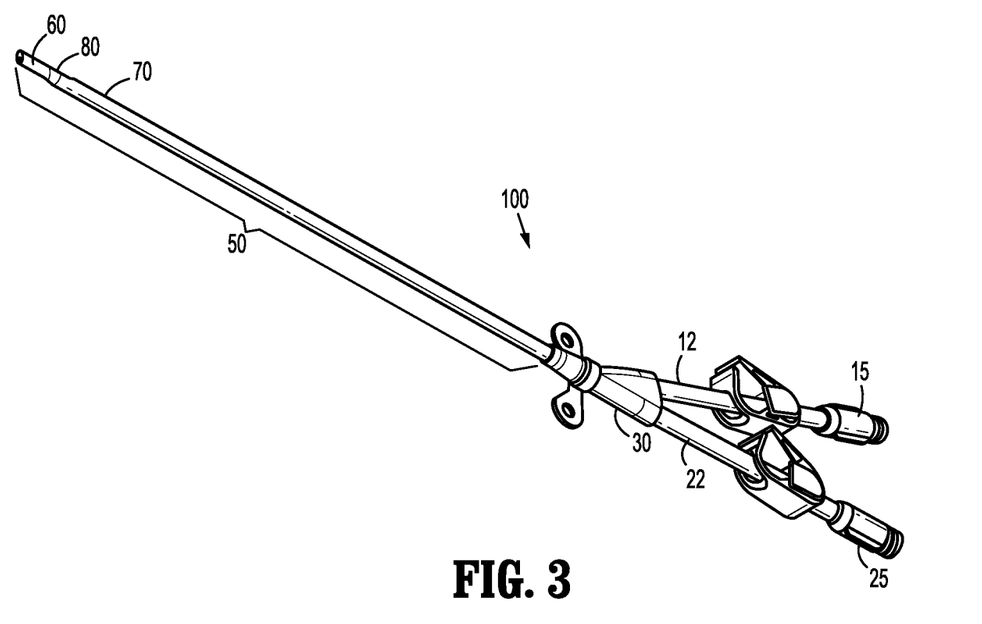
FIG. 3 is an oblique view seen from a further different angle of the overall structure of the dialysis catheter as shown in FIG. 1.
Figure 4:
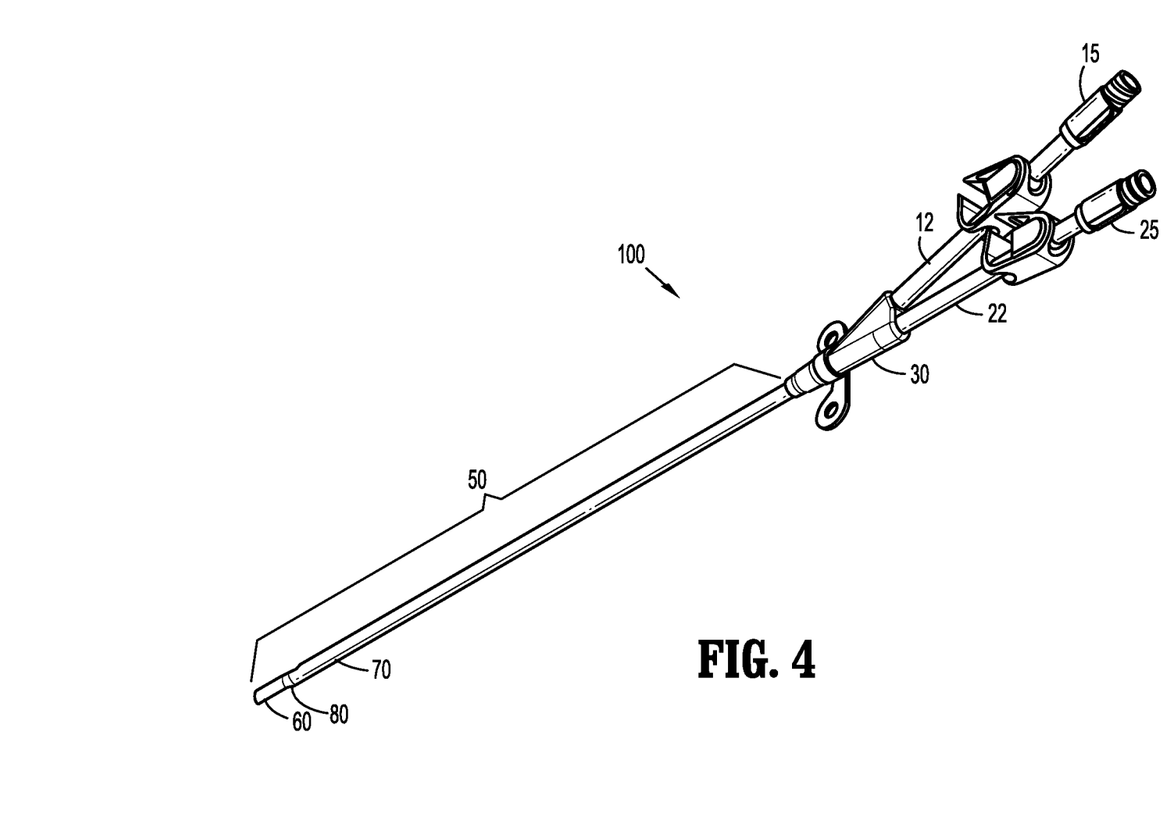
FIG. 4 is an oblique view seen from yet another different angle of the overall structure of the dialysis catheter as shown in FIG. 1.
Figure 5:
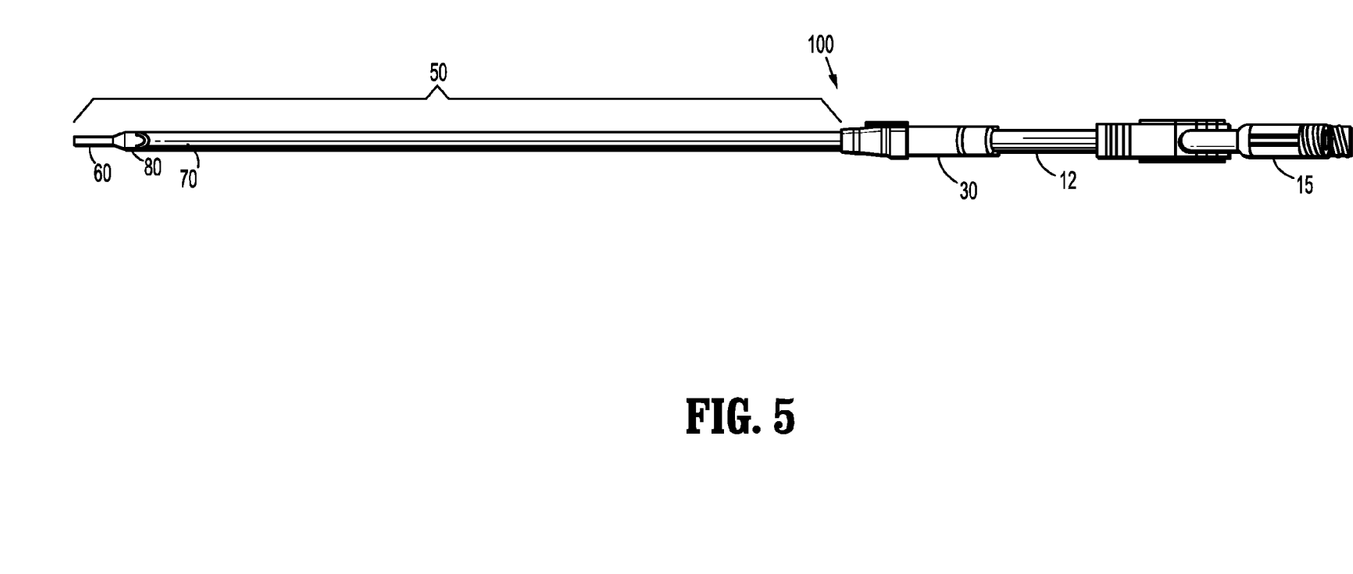
FIG. 5 is a plan view of the dialysis catheter of FIG. 1.
Figure 6:
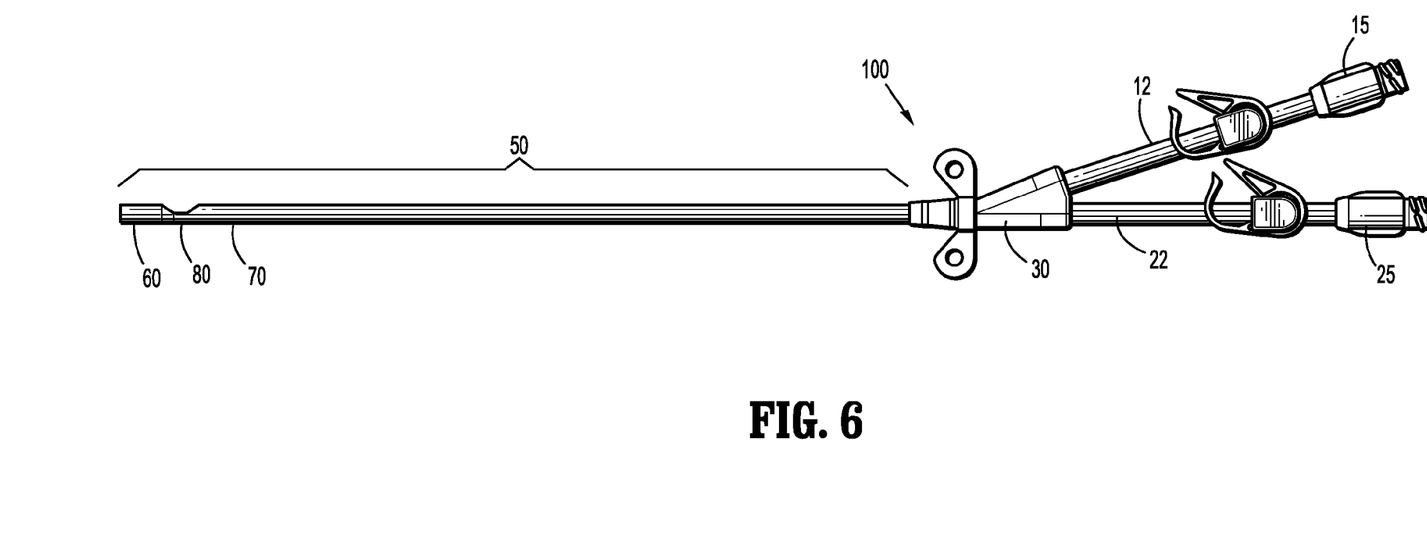
FIG. 6 is a view from the right-hand side of the dialysis catheter as shown in FIG. 1.
Figure 7:
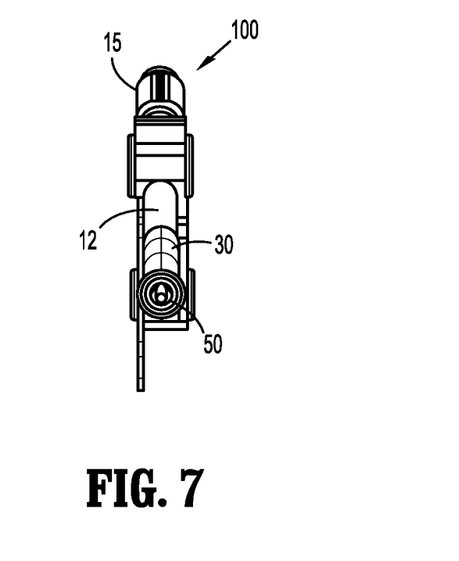
FIG. 7 is a front view of the dialysis catheter of FIG. 1.
Figure 8:
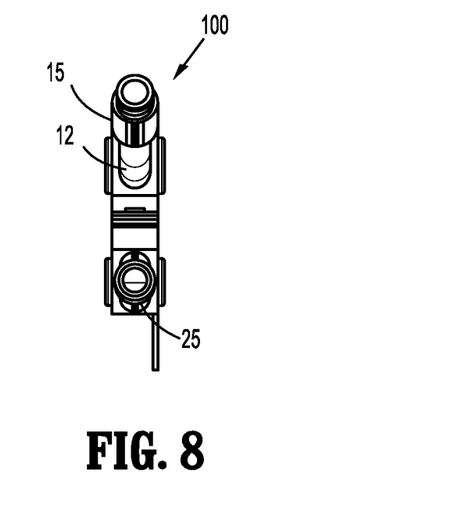
FIG. 8 is a back view of the dialysis catheter of FIG. 1.
Figure 9:
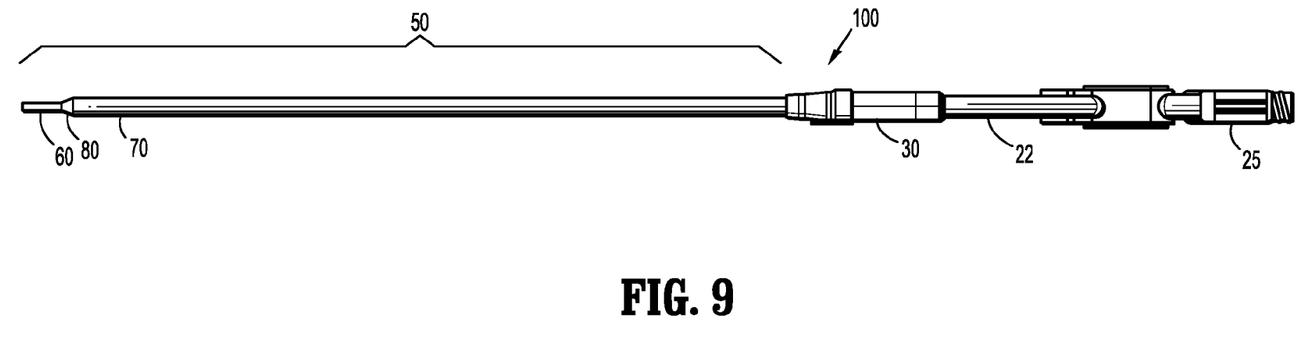
FIG. 9 is a bottom view of the dialysis catheter of FIG. 1.

FIG. 1 is an oblique view showing the overall structure of a dialysis catheter 100 (referred to below simply as the "catheter 100") according to a mode of embodiment of the present disclosure. FIG. 2 is an oblique view seen from a different angle of the overall structure of the catheter 100. FIG. 3 is an oblique view seen from another different angle of the overall structure of the catheter 100. FIG. 4 is an oblique view seen from yet another different angle of the catheter 100. FIG. 5 is a plan view of the catheter 100. FIG. 6 is a view from the right-hand side of the catheter 100. FIG. 7 is a front view of the catheter 100. FIG. 8 is a back view of the catheter 100. FIG. 9 is a bottom view of the catheter 100.

The overall structure and action of the catheter 100 will be described with reference to FIGS. 1 to 9. The catheter 100 is employed for blood dialysis in which some of a patient's blood is circulated by making the catheter indwelling in a target blood vessel (a large-diameter blood vessel which has a plentiful flow of blood, such as the femoral vein or the subclavian vein, for example) using the Seldinger technique, for example, extracting blood (removing blood) to outside the body (dialysis circuit), removing waste materials and toxins in the dialysis circuit, and delivering the blood (feeding the blood) into the blood vessel. It should be noted that a view from the left-hand side of the catheter 100 has been omitted because it would be the same as the view from the right-hand side shown in FIG. 6.

The catheter 100 has a catheter body 50 including a tube whereof the cavity is partitioned by means of a dividing wall 51 into a two-layer lumen (blood removal lumen 10, blood feed lumen 20). The catheter 100 is an end-hole type double-lumen catheter in which tip-end openings (a blood removal hole 11 and a blood feed hole 21) are provided at the tip end of the catheter body 50 thereof. Furthermore, the catheter 100 is designed in such a way that the tip end of the blood removal lumen 10 is positioned further towards the base end than the tip end of the blood feed lumen 20, in other words the tip end of the blood feed lumen 20 projects forwards from the tip end. It should be noted that the tip-end side refers to the side which is inserted into the blood vessel, and the base-end side refers to the side which is connected to the dialysis circuit.

The catheter 100 includes, in addition to the catheter body 50, a split part 30, a blood removal branch pipe 12, and a blood feed branch pipe 22. That is to say, the catheter 100 is designed in such a way that the blood removal lumen 10 is connected to an external dialysis circuit (not depicted) by way of the split part 30 and the blood removal branch pipe 12, while the blood feed lumen 20 is connected to the external dialysis circuit by way of the split part 30 and the blood feed branch pipe 22.

The catheter body 50 may be formed from a material such as polyurethane, polyvinyl chloride, silicone or polyamide, for example. It should be noted that no particular limitation is imposed as to the material from which the catheter body 50 is made, but the material which is used should be hard enough to retain a stable shape inside the blood vessel but should not damage the blood vessel. It is known that among these materials, polyurethane is the preferred material for the catheter body 50. This is because polyurethane has the combined features of sufficient strength for there to be no reduction in ease of insertion of the catheter into the body and flexibility at body temperature when inserted.

The split part 30 includes flow paths which provide communication between the catheter body 50 which is indwelling in the blood vessel and each of the branch pipes (blood removal branch pipe 12, blood feed branch pipe 22). That is to say, the split part 30 serves to place each of the plurality of branch pipes in communication with each of the lumens of the catheter body 50. The catheter 100 is therefore designed in such a way that the blood removal lumen 10 is connected to the blood removal branch pipe 12 by way of the split part 30, and the blood feed lumen 20 is connected to the blood feed branch pipe 22 by way of the split part 30, and the flow paths (blood removal flow path, blood feed flow path) do not communicate with each other. The split part 30 may be formed, for example, by inserting rod-like members into the lumens of the catheter body 50 from the open ends of the branch pipes, mounting the assembly in a mould, injecting molten synthetic resin from a resin injection port formed in the mould, and, after the synthetic resin has cured, removing the mould and withdrawing the rod-like members.

The blood removal branch pipe 12 includes a tube which can be connected to the split part 30. A blood removal-side connector 15 is fitted to the base end of the blood removal branch pipe 12. The external dialysis circuit is therefore connected to the blood removal branch pipe 12 by way of the blood removal-side connector 15. The blood feed branch pipe 22 includes a tube which can be connected to the split part 30. A blood feed-side connector 25 is fitted to the base end of the blood feed branch pipe 22. The external dialysis circuit is therefore connected to the blood feed branch pipe 22 by way of the blood feed-side connector 25.

The blood removal branch pipe 12 and the blood feed branch pipe 22 may be formed from the same material as the catheter body 50 or from a different material. However, the blood removal branch pipe 12 and the blood feed branch pipe 22 are generally formed from a material which is strong enough for the cavity therein not to be closed off even if said branch pipes are bent and which has properties such as not to damage the surface of the skin. Examples of such a material which may be mentioned include polyurethane, polyvinyl chloride, silicone and polyamide, for example.

The blood removal-side connector 15 and the blood feed-side connector 25 may be designed in such a way that the branch pipes (blood removal branch pipe 12 and blood feed branch pipe 22) can be easily connected to external equipment (tubes which are connected to the dialysis circuit, other connectors, syringes, etc.). Furthermore, the blood removal-side connector 15 and the blood feed-side connector 25 may be formed from a synthetic resin having high hardness, strength, drug resistance and morphological stability. Examples of such a material which may be mentioned include polycarbonate and hard polyvinyl chloride, polyurethane, polyamide, polyetherimide and polyacetal etc., for example. It is also possible to use mixtures in which other additives have been mixed with the above synthetic resins.

It should be noted that no particular limitation is imposed in terms of the structure of the blood removal-side connector 15 and the blood feed-side connector 25, but this structure may include a female luer connector (or male luer connector) which can be attached to a male luer connector (or female luer connector), for example. Furthermore, it is equally feasible to employ a blood removal-side connector 15 and a blood feed-side connector 25 provided with a screw-type locking mechanism, such as that shown in FIG. 1, in order to provide a reliable connection with the external equipment. In addition, a clamping member such as a lock ring may be separately provided in order to enable connection with the external equipment.

Furthermore, the catheter 100 is such that the functions of the blood removal branch pipe 12 and the blood feed branch pipe 22 may be switched for use. In this case, the functions of the blood removal lumen 10 and the blood feed lumen 20 are also switched. That is to say, the blood removal branch pipe 12 and the blood removal lumen 10 are described in terms of removing blood and the blood feed branch pipe 22 and the blood feed lumen 20 are described in terms of feeding blood, but the functions may be switched for use in the event of blood removal failure or the like (this switching is known as reverse connection).

The action of the catheter 100 will now be described.

When blood dialysis is performed, the catheter 100 is made indwelling in the target blood vessel using the Seldinger technique, for example. That is to say, a guidewire (not depicted) which is inserted into the target blood vessel is inserted from the tip end opening of a stylet (not depicted) which is inserted into the blood feed lumen 20 of the catheter body 50 of the catheter 100, and the catheter body 50 is pushed forward along the guidewire together with the stylet in order to insert the catheter body 50 into the blood vessel. However, the resistance to insertion of the catheter into the body is preferably low so that the inside of the body is not damaged by the catheter body 50 during the time until the catheter 50 is inserted in the blood vessel. It should be noted that it is possible to smoothly insert the catheter body 50 into the blood vessel by using a stylet, but it is still possible to insert the catheter body 50 into the blood vessel without using a stylet.

The tip end of the catheter body 50 is then oriented in the same direction as the flow of blood, and the guidewire and stylet are withdrawn in order to make the catheter body 50 indwelling in the blood vessel. After this, the blood removal lumen 10 and the blood feed lumen 20 are each connected to the external dialysis circuit by way of the blood removal-side connector 15 and blood feed-side connector 25, respectively. In this state, blood flowing in the blood vessel can be removed by way of the blood removal hole 11 in the blood removal lumen 10, and blood which has been purified in the external dialysis circuit can be fed into the blood vessel through the blood feed hole 21 in the blood feed lumen 20.

A suction force is produced at the blood removal hole 11 during blood dialysis, and therefore the blood removal hole 11 may be sucked onto the blood vessel wall. Furthermore, the suction force is produced at the blood removal hole 11 during blood dialysis, and therefore a blood clot or fibrin sheath may close off the blood removal hole 11 or blood removal lumen 10. Blood removal failure occurs if these situations arise, which leads to poorer dialysis efficiency. When blood removal failure occurs during dialysis, it is conventional practice to apply a suction pressure to the blood removal lumen using a syringe or to connect a syringe filled with physiological saline and repeatedly inject this and remove blood, these measures being designed to remove a blood clot or fibrin sheath by collecting the clot or sheath inside the syringe. Blood removal failure may be eliminated in this manner, but eliminating blood removal failure is not such a simple issue.

The catheter 100 is designed in such a way that there is no deterioration of the dialysis efficiency because the occurrence of the "clinging phenomenon", which is a cause of blood removal failure, is suppressed. That is to say, the catheter 100 makes it possible to improve patency without a reduction in ease of insertion of the catheter into the body by virtue of an improved shape at the tip end of the catheter body 50, and also makes it possible to effectively suppress the occurrence of the "clinging phenomenon" in which the blood removal hole 11 attaches to the blood vessel wall and ends up being closed off. The tip-end shape of the catheter body 50 will be described in detail below.

Figure 10:
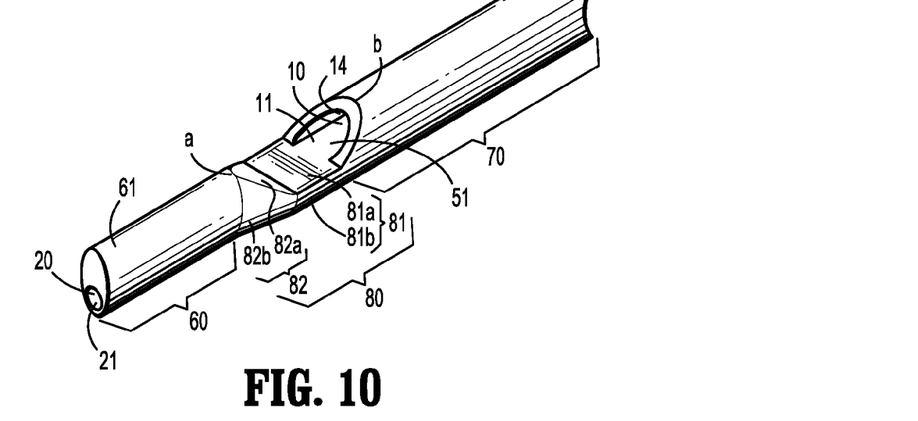
FIG. 10 is an enlarged oblique view showing an enlargement of the region X in FIG. 1.
Figure 11:
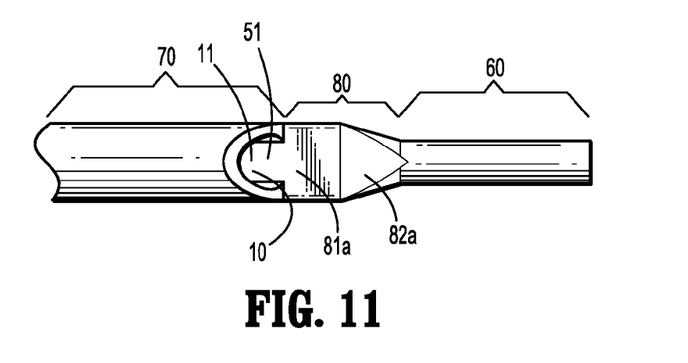
FIG. 11 is an enlarged plan view showing an enlargement of the region X in FIG. 1.
Figure 12:
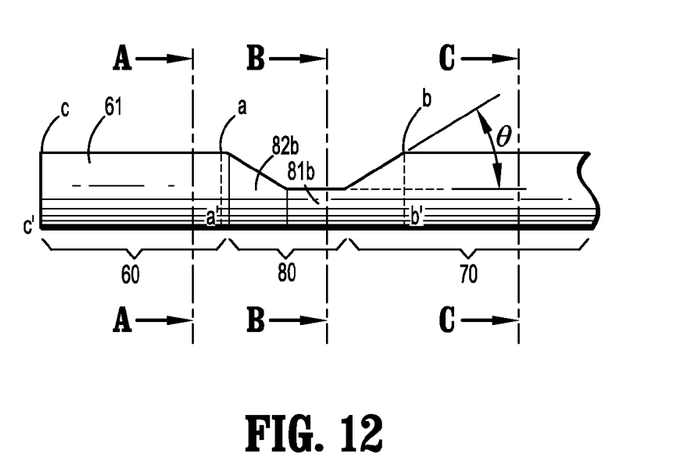
FIG. 12 is an enlarged view from the right-hand side showing an enlargement of the region X in FIG. 1.
Figure 13:
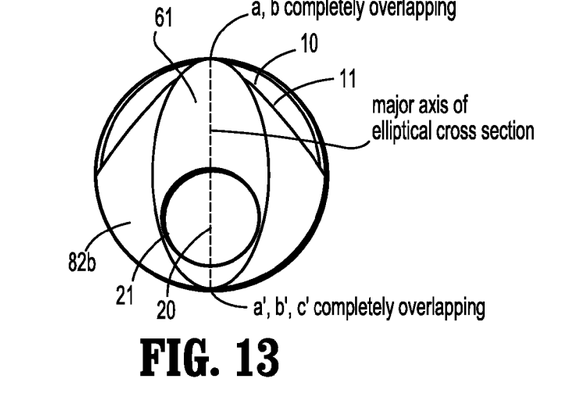
FIG. 13 is an enlarged front view showing a state seen from the tip-end side of the region X in FIG. 1.
Figure 14:
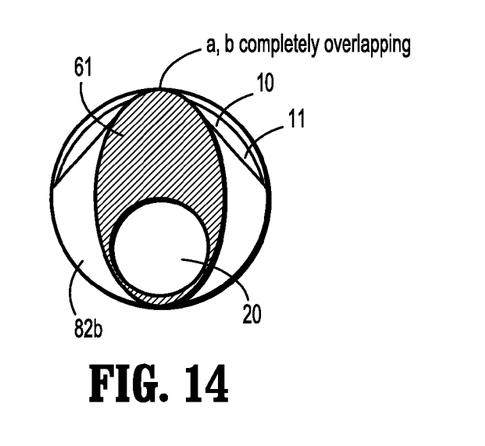
FIG. 14 is a view seen along the arrows of the cross section A-A in FIG. 12.
Figure 15:
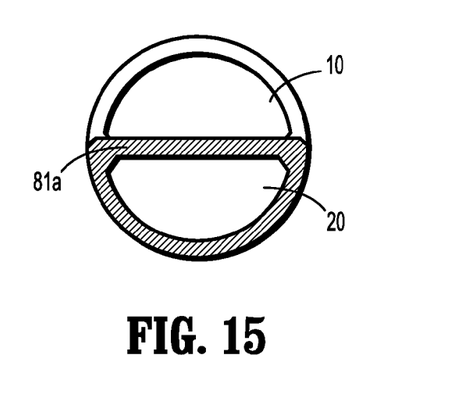
FIG. 15 is a view seen along the arrows of the cross section B-B in FIG. 12.
Figure 16:
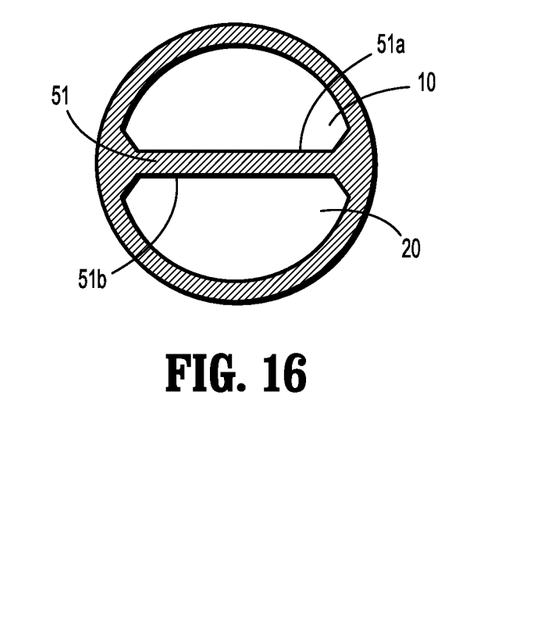
FIG. 16 is a view seen along the arrows of the cross section C-C in FIG. 12.
Figure 17:
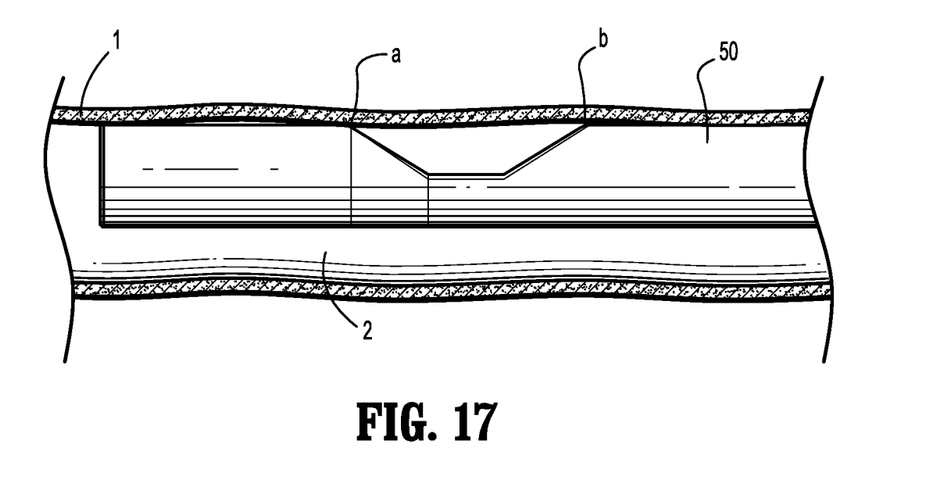
FIG. 17 is a diagram schematically showing the situation when the catheter body has been inserted in a blood vessel.

FIG. 10 is an enlarged oblique view showing an enlargement of the region X in FIG. 1. FIG. 11 is an enlarged plan view showing an enlargement of the region X in FIG. 1. FIG. 12 is an enlarged view from the right-hand side showing an enlargement of the region X in FIG. 1. FIG. 13 is an enlarged front view showing a state seen from the tip-end side of the region X in FIG. 1. FIG. 14 is a view seen along the arrows of the cross section A-A in FIG. 12. FIG. 15 is a view seen along the arrows of the cross section B-B in FIG. 12. FIG. 16 is a view seen along the arrows of the cross section C-C in FIG. 12. FIG. 17 is a diagram schematically showing the situation when the catheter body 50 has been inserted in a blood vessel 2. The tip-end shape of the catheter body 50 will be described in detail, along with the advantages thereof, with reference to FIGS. 10-17. It should be noted that the enlarged plan view in FIG. 11, the enlarged view from the right-hand side in FIG. 12 and the enlarged front view in FIG. 13 correspond to the plan view in FIG. 5, the view from the right-hand side in FIG. 6 and the front view in FIG. 7, respectively.

The blood removal lumen 10 and the blood feed lumen 20 which are partitioned by means of the dividing wall 51 are formed in the catheter body 50 so as to run alongside each other. That is to say, one of the surfaces of the dividing wall 51 (the surface 51a shown in FIG. 16) forms part of the inner wall of the blood removal lumen 10, while the other surface of the dividing wall 51 (the surface 51b in FIG. 16) forms part of the inner wall of the blood feed lumen 20. The catheter body 50 is characterized in particular by the shape at the tip end (first portion 60, third portion 80), including the blood feed lumen 20, from the blood removal hole 11 up to the blood feed hole 21. It should be noted that the length from the tip end of the catheter body 50 up to the area where the blood removal hole 11 is formed, i.e. the combined length in the flow path direction of the first portion 60 and the third portion 80 is 20 mm-40 mm.

The catheter body 50 includes: the first portion 60 which includes the blood feed lumen 20 and lies at the tip end within the area between the blood removal hole 11 and the blood feed hole 21; a second portion 70 including the blood feed lumen 20 and the blood removal lumen 10, whereof the cross-sectional shape from the blood removal hole 11 to the base end is substantially circular; and the third portion 80 which includes the blood feed lumen 20 and connects the first portion 60 and the second portion 70. It should be noted that the cross section refers to the surface substantially perpendicular to the flow path direction, this being a surface which is formed when the catheter body 50 is cut longitudinally (and the same meaning below).

The first portion 60 is the portion which includes the blood feed lumen 20 and is formed to a prescribed length from the tip end within the area between the blood removal hole 11 and the blood feed hole 21. The first portion 60 is provided with a thickened part 61 which increases the thickness of the peripheral wall of the blood feed lumen 20 on the blood removal lumen 10 side. The cross-sectional area of the first portion 60 including the thickened part 61 (the cross-sectional area including the space (blood feed lumen 20) portion, the same below) is less than the cross-sectional area of the second portion 70 (the cross-sectional area including the space (blood removal lumen 10, blood feed lumen 20) portion, the same below). That is to say, the first portion 60 of the catheter body 50, including the thickened part 61, has a narrower shape than the second portion 70 thereof, which makes it possible to suppress resistance to insertion of the catheter into the body. It should be noted that the cross-sectional area of the first portion 60 including the thickened part 61 should be no more than around 60% of the cross-sectional area of the second portion 70. Furthermore, the length of the first portion 60 in the flow path direction should be 5 mm-30 mm.

The second portion 70 is the portion including the blood feed lumen 20 and the blood removal lumen 10, whereof the cross-sectional shape from the blood removal hole 11 to the base end is substantially circular. The second portion 70 is formed in such a way that the cavity of a single tube is partitioned by means of the dividing wall 51 so that the blood removal lumen 10 and the blood feed lumen 20 run alongside each other. Accordingly, the cross-sectional shape of the second portion 70 is substantially circular (see FIG. 16).

The third portion 80 includes an extension part 81 including a flat surface part 81*a* provided at the base-end side as an extension of the dividing wall 51 and forming part of the peripheral wall of the blood feed lumen 20, and a curved surface part 81*b* forming part of the peripheral wall of the blood feed lumen 20 outside the extended dividing wall 51. The extension part 81 is shaped like the second portion 70 with the blood removal lumen 10 removed therefrom, in other words it has a substantially semicircular cross-sectional shape. It should be noted that the length of the third portion 80 in the flow path direction should be determined so as to be 20 mm-40 mm, which was mentioned above, when combined with the length of the first portion 60 in the flow path direction.

Furthermore, the third portion 80 includes a connecting part 82 for connecting the extension part 81 and the first portion 60. The connecting part 82 includes a first inclined face 82*a* which connects the top part a and surrounding area of the thickened part 61 of the first portion 60 to the flat surface part 81*a* of the extension part 81; and a second inclined face 82*b* which connects the peripheral wall of the first portion 60, other than the top part a and surrounding area of the thickened part 61, to the curved surface part 81*b* of the extension part 81. This means that the cross-sectional shape of the blood removal lumen 10 (the cross-sectional area including the space (blood removal lumen 10) portion) is a largely constant shape, while the cross-sectional shape of the blood feed lumen 20 (the cross-sectional area including the space (blood feed lumen 20) portion) links up with the connecting part 82. That is to say, the blood feed lumen 20 reaches the blood feed hole 21 with the diameter thereof being reduced at the connecting part 82.

The first inclined face 82*a* expands from the top part a and surrounding area of the thickened part 61 of the first portion 60 towards the flat surface part 81*a* of the extension part 81. That is to say, the first inclined face 82*a* has a substantially triangular shape wherein the top part a and surrounding area of the thickened part 61 form the vertex (see FIG. 11). The second inclined face 82*b* is formed in such a way that, when seen from the side, the height increases (the length increases) towards the tip end (this height being the length of an imaginary straight line running substantially parallel to the section where the curved surface part 81*b* and the first portion 60 are connected). That is to say, the second inclined face 82*b* has a substantially trapezoidal shape, when seen from the side, wherein the section which is connected to the curved surface part 81*b* forms the upper base and the section which is connected to the first portion 60 forms the lower base, with the upper base being shorter than the lower base (see FIG. 12).

Furthermore, the catheter body 50 is designed in such a way that, when the catheter body 50 is seen from the tip-end side, the top part a of the thickened part 61 of the first portion 60 and the top part b at the outer periphery of the blood removal hole 11, which has a substantially semicircular cross section in the second portion, completely overlap each other. The shape of the thickened part 61 includes the top part in the cross section thereof (substantially semicircular cross-sectional shape or substantially semielliptical cross-sectional shape, or similar, for example), and the length of the thickened part 61 in the flow path direction is the same as the length of the first portion 60. Furthermore, when the thickened part 61 is seen from the side, it may have a shape such that the straight line linking the top part a and a top part c at the tip end is inclined upwards towards the base end so that the tip-end side is narrower. That is to say, the outer shape of the first portion 60 including the thickened part 61 may be a substantially tapered shape wherein the cross-sectional area becomes gradually larger from the tip end up to the section which is connected to the third portion 80.

For example, the cross-sectional shape of the first portion 60 including the thickened part 61 may be a substantially elliptical shape in which the major axis is substantially perpendicular to the dividing wall 51, and the major axis of the substantially elliptical shape is made to substantially coincide with the diameter of the second portion 70 which has a substantially circular cross-sectional shape (see FIG. 13). When the catheter body 50 is seen from the tip-end side in this case, the top part a of the thickened part 61 and the top part b at the outer periphery of the blood removal hole 11 are completely overlapping. Furthermore, when the catheter body 50 is seen from the tip-end side, the portions of the top part a, top part b and top part c lying on the respective opposite sides thereof (see the bottom of FIG. 12) (these portions are denoted a', b', c') are also completely overlapping. That is to say, the a', b', c' side of the blood feed lumen 20 forms a straight line passing through the first portion 60, second portion 70 and third portion 80. It should be noted that there is no particular limitation as to the length of the minor axis when the cross-sectional shape of the first portion 60 including the thickened part 61 is substantially elliptical.

That is to say, the catheter 100 is such that most of the blood removal hole 11 is covered by the first portion 60 when the catheter body 50 is seen from the tip-end side. This means that it is possible to cover the open face 14 of the blood removal hole 11 with the first portion 60, which produces resistance when the catheter is inserted into the body, and resistance to insertion of the catheter body 50 into the body is reduced. Furthermore, with the catheter 100, the open face 14 of the blood removal hole 11 is inclined towards the base end, in other words inclined in such a way that the angle formed by the open face 14 of the blood removal hole 11 and the dividing wall 51 (the angle θ shown in FIG. 12) is an acute angle, and therefore insertion resistance can be further reduced. As shown in FIG. 17, even if the catheter body 50 is inserted into the blood vessel 2 and the blood removal hole 11 approaches the blood vessel wall 1, the thickened part 61 of the first portion 60 acts as a barrier which makes it possible to suppress contact of the blood removal hole 11 with the blood vessel wall 1. This means that it is possible to markedly reduce the occurrence of the "clinging phenomenon" which causes blood removal failure.

It is also possible to control the bending direction of the catheter body 50 in the blood vessel if the first portion 60 including the thickened part 61 has a substantially elliptical cross-sectional shape. That is to say, it is possible to make it more difficult for the first portion 60 to bend in the major axis direction, and the actual approach of the blood removal hole 11 to the blood vessel wall can be controlled from the outset. The catheter 100 therefore makes it possible to markedly reduce the occurrence of the "clinging phenomenon" which causes blood removal failure, without any reduction in patency.

It should be noted that the catheter 100 is an end-hole type double-lumen catheter, and therefore it has the feature of excellent patency. That is to say, the blood removal hole 11 is formed so as to face the tip end, i.e. the blood flow direction, rather than the side surface of the blood removal lumen 10, and so the catheter has the feature that the blood removal hole 11 or the blood removal lumen 10 is less likely to be closed off by a blood clot or fibrin sheath.

As described above, use of the catheter 100 makes it possible to improve patency without any reduction in ease of insertion of the catheter into the body, and also to effectively suppress the occurrence of the "clinging phenomenon" in which the blood removal hole 11 attaches to the blood vessel wall and ends up being closed off. Furthermore, although the catheter 100 can be used as either a long-term indwelling catheter or a short-term indwelling catheter, it is extremely effective in situations requiring more immediacy. In addition, the catheter 100 can be formed without the need for complex structures. The catheter 100 is therefore extremely simple to use and makes it possible to markedly lighten the burden on the practitioner and the patient.

What is claimed is:

1. A dialysis catheter comprising:
a catheter body including a blood feed lumen and a blood removal lumen partitioned by a dividing wall, the blood feed lumen including a blood feed hole formed at a tip end of the blood feed lumen and the blood removal lumen including a blood removal hole formed at a tip end of the blood removal lumen, the tip end of the blood removal lumen being positioned proximal to the tip end of the blood feed lumen towards a base end of the catheter body, the catheter body comprising:
a first portion including the blood feed lumen formed to a prescribed length from a tip-end side of the catheter body within an area between the blood removal hole and the blood feed hole, the first portion comprising a thickened part;
a second portion proximal of the blood removal hole including the blood feed lumen and the blood removal lumen, the second portion including a cross-sectional shape from the blood removal hole to the base end which is substantially circular, and a cross-sectional area of the first portion including the thickened part is less than a cross-sectional area of the second portion; and
a third portion connecting the first portion and the second portion, the third portion comprising an extension part having a substantially semicircular cross-sectional shape and including a flat surface part provided as an extension of the dividing wall and forming part of a peripheral wall of the blood feed lumen, and a curved surface part forming part of a peripheral wall of the blood feed lumen outside the dividing wall, and a connecting part for connecting the extension part and the first portion,
wherein a top part of the thickened part on the first portion and a top part of the blood removal hole which has a substantially semicircular cross section in the second portion overlap each other when the catheter body is seen from the tip-end side.

2. The dialysis catheter according to claim 1, wherein a cross-section of the first portion has a substantially elliptical shape in which a major axis is substantially perpendicular to the dividing wall, and the major axis of the substantially elliptical shape is made to substantially coincide with a diameter of the cross-sectional shape of the second portion.

3. The dialysis catheter according to claim 1, wherein the connecting part of the third portion comprises:
a first inclined face which connects an area around the top part of the thickened part to the flat surface part of the extension part; and
a second inclined face which connects the peripheral wall of the first portion, other than the area around the top part of the thickened part, to the curved surface part of the extension part.

4. The dialysis catheter according to claim 1, wherein the open face of the blood removal hole is inclined to form an acute angle with the dividing wall.

* * * * *